(12) United States Patent
Sun et al.

(10) Patent No.: US 9,340,762 B2
(45) Date of Patent: May 17, 2016

(54) METHOD FOR AUTOMATED SPERM MANIPULATION AND DEVICE FOR HOLDING SPERM AND OOCYTES

(76) Inventors: Yu Sun, Toronto (CA); Zhe Lu, Toronto (CA); Clement Leung, Vancouver (CA); Xuping Zhang, Toronto (CA)

(*) Notice: Subject to any disclaimer, the term of this patent is extended or adjusted under 35 U.S.C. 154(b) by 167 days.

(21) Appl. No.: 13/817,828

(22) PCT Filed: Aug. 19, 2011

(86) PCT No.: PCT/CA2011/000930
§ 371 (c)(1), (2), (4) Date: Feb. 20, 2013

(87) PCT Pub. No.: WO2012/037642
PCT Pub. Date: Mar. 29, 2012

(65) Prior Publication Data
US 2013/0143200 A1    Jun. 6, 2013

Related U.S. Application Data
(60) Provisional application No. 61/375,503, filed on Aug. 20, 2010.

(51) Int. Cl.
*C12M 1/34* (2006.01)
*C12M 3/00* (2006.01)
(Continued)

(52) U.S. Cl.
CPC ............... *C12M 21/06* (2013.01); *C12M 23/12* (2013.01); *C12M 23/28* (2013.01); *C12M 23/34* (2013.01); *C12M 41/48* (2013.01); *C12Q 1/24* (2013.01); *C12Q 3/00* (2013.01)

(58) Field of Classification Search
CPC ...... C12M 21/06; C12M 23/16; C12M 41/48; C12N 5/0604; C12N 5/0609; C12N 5/061; C12N 15/873; C12N 15/89; G01N 33/5029
See application file for complete search history.

(56) References Cited

U.S. PATENT DOCUMENTS
4,176,953 A    12/1979    Bartoov et al.
4,402,614 A    9/1983     Porath-Furedi
(Continued)

FOREIGN PATENT DOCUMENTS
DE    19803651 A1    11/1999
EP    1595941 A2     11/2005
(Continued)

OTHER PUBLICATIONS
Shi et al. "Real-Time Automated Tracking and Trapping System for Sperm". Microscopy Research and Techniques, vol. 69 (2006), pp. 894-902.*
(Continued)

*Primary Examiner* — William H Beisner
(74) *Attorney, Agent, or Firm* — Eduardo Krupnik; Miller Thomson LLP

(57) ABSTRACT

The present invention relates to systems and methods for automated, computer-controlled, tracking and manipulation of motile specimen. The systems and methods of the present invention are suited for tracking and manipulating sperm, particularly for Intracytoplasmic Sperm Injection (ICSI) procedures. The present invention also relates also to devices for holding motile cells, such as sperm, and non-motile cells, such as oocytes. The device of the present invention comprises a sealed chamber having an air outlet, one well for the motile cells, and another well for non-motile cells.

6 Claims, 10 Drawing Sheets

(51) Int. Cl.
*C12Q 1/24* (2006.01)
*C12Q 3/00* (2006.01)
*C12M 1/32* (2006.01)
*C12M 1/00* (2006.01)
*C12M 1/36* (2006.01)

(56) References Cited

U.S. PATENT DOCUMENTS

| | | | |
|---|---|---|---|
| 4,896,966 | A | 1/1990 | Boisseau et al. |
| 4,896,967 | A | 1/1990 | Douglas-Hamilton et al. |
| 5,262,128 | A | 11/1993 | Leighton et al. |
| 6,641,526 | B1 * | 11/2003 | Wakayama et al. ............ 600/33 |
| 7,042,639 | B1 | 5/2006 | McDowell |
| 7,106,502 | B1 | 9/2006 | McDowell |
| 7,252,642 | B2 | 8/2007 | Kislev |
| 7,268,939 | B1 | 9/2007 | McDowell |
| 7,521,696 | B2 | 4/2009 | Courtney et al. |
| 7,526,116 | B2 | 4/2009 | Armogida |
| 7,720,272 | B2 | 5/2010 | Armogida |
| 7,758,811 | B2 | 7/2010 | Durack et al. |
| 7,799,569 | B2 | 9/2010 | Durak et al. |
| 7,838,210 | B2 | 11/2010 | Ludwig et al. |
| 7,855,078 | B2 | 12/2010 | Evans |
| 7,875,845 | B2 | 1/2011 | Plewa et al. |
| 7,943,384 | B2 | 5/2011 | Durack et al. |
| 2004/0146848 | A1 | 7/2004 | Kislev et al. |
| 2005/0250197 | A1 | 11/2005 | Ando et al. |
| 2007/0048857 | A1 | 3/2007 | Ito et al. |
| 2007/0245812 | A1 | 10/2007 | Kislev et al. |
| 2010/0046823 | A1 | 2/2010 | O Ruanaidh et al. |
| 2011/0061472 | A1 | 3/2011 | Wo et al. |
| 2011/0147591 | A1 | 6/2011 | Kislev et al. |
| 2011/0149287 | A1 | 6/2011 | Kislev et al. |
| 2011/0250690 | A1 * | 10/2011 | Craig ............................ 435/404 |

FOREIGN PATENT DOCUMENTS

| | | | |
|---|---|---|---|
| EP | 1752221 | A1 | 2/2007 |
| WO | 2008034249 | A1 | 3/2008 |
| WO | WO 2010022391 | A2 * | 2/2010 |
| WO | WO 2010056755 | A2 * | 5/2010 |
| WO | 2010115167 | A2 | 10/2010 |

OTHER PUBLICATIONS

Tesarik et al. "Human oocyte activation after intracytoplasmic sperm injection". Human Reproduction, vol. 9, No. 3 (1994), pp. 511-518.*

Baba et al. "An Approach to Digital Image Analysis fo Bending Shapes of Eukaryotic Flagella and Cilia." Cell Motility, vol. 5 (1985), pp. 475-489.*

Mortimer et al. "Quantitative observations of flagellar motility of capacitating human spermatozoa." Human Reproduction, vol. 12, No. 5 (1997), pp. 1006-1012.*

Shi, Linda et al, An automatic system to study sperm motility and energetics, Biomed Microdevices, Feb. 2008, p. 573-583, v. 10, Springer Science and Business Media, LLC.

Amann, Rupert et al, Reflections on CASA After 25 Years, Journal of Andrology, 2004, p. 317-325, v. 25, No. 3, American Society of Andrology.

Oku, Hiromasa et al, How to Track Spermatozoa using High-Speed Visual Feedback, 30th Annual International IEEE EMBS Conference, Aug. 2008, p. 125-128, IEEE.

Berezansky, Michael et al, Segmentation and Tracking of Human Sperm Cells using Spatio-Temporal Representation and Clustering, Proc. of SPIE, 2007, vol. 6512, Medical Imaging.

Shi, Linda et al, Computer-based tracking of single sperm; Journal of Biomedical Optics, Oct. 2006, p. 1-10, vol. 11, No. 5.

Lu, Zhe et al, Robotic ICSI (Intracytoplasmic Sperm Injection), IEEE Transactions on Biomedical Engineering, Jul. 2011, p. 2102-2108, vol. 58, No. 7, IEEE.

Leung, Clement et al, Automated Sperm Immobilization for Intracytoplasmic Sperm Injection, IEE Transactions on Biomedical Engineering, Apr. 2011, p. 935-942, vol. 58, No. 4, IEEE.

Liu, Xinyu et al, Automated Microinjection of Recombinant BCL-X into Mouse Zygotes Enhances Embryo Development, PLoS One, Jul. 2011, p. 1-10, vol. 6, Issue 7.

* cited by examiner

METHOD FOR AUTOMATED SPERM MANIPULATION AND DEVICE FOR HOLDING SPERM AND OOCYTES

CROSS REFERENCE TO RELATED APPLICATIONS

This application is a national stage application under 35 U.S.C. 371 of International Application No. PCT/CA2011/000930, filed Aug. 19, 2011, which in turn claims the benefit under 35 U.S.C. 119(e) of U.S. Provisional Ser. No. 61/375,503, filed Aug. 20, 2010, the contents of each of which are hereby incorporated by reference into the present disclosure.

FIELD OF INVENTION

The present invention relates to systems and methods for automated tracking and manipulation of motile specimen. The present invention also relates to devices for holding motile cells and non-motile cells.

BACKGROUND OF THE INVENTION

Sperm manipulation is widely used in clinical practice and research, using a small-sized tool (e.g., micropipette) to interact with a sperm. For example, in Intracytoplasmic Sperm Injection (ICSI), a medical procedure for in vitro fertilization, a sperm is tapped/immobilized by a micropipette, aspirated into the micropipette, and dispensed from the micropipette into an oocyte (i.e., egg cell).

Conventionally, sperm manipulation is performed manually. An operator controls the motion of a micropipette via a joy stick to physically tap/manipulate the sperm under an optical microscope. Sperm immobilization requires a micropipette to press (tap) the sperm tail against a surface (e.g., the bottom of a Petri dish). As such, sperm immobilization can be a challenging procedure that has stringent skill requirements. Due to the fast movement of a healthy sperm (25 µm/sec), a sperm can move out of the field of view of a microscope quickly. The operator needs to carefully monitor the motion of the sperm by looking into the eye pieces of a microscope and manually move the microscope stage to keep the sperm within the field of view, while simultaneously attempting to move the micropipette to tap the sperm tail (under 1 µm in thickness) for immobilization.

Different from the use of a micropipette for sperm manipulation, EPO Pat. Publ. No. 19803651 discloses a method that uses a pulsed laser to immobilize sperm in culture medium. This method provides an alternative approach for sperm immobilization, but does not automate the sperm immobilization procedure. It also does not enable other operations such as aspiration and dispensation of a sperm. U.S. Pat. No. 7,875,845 discloses a system that uses optical tweezers to move microscopic particles (e.g., sperm) between different regions of the system. PCT Publ. No. WO2010115167 discloses a system that uses dielectrophoresis (DEP) fields for extracting and separating microscopic particles (e.g., sperm).

Assisted analysis of sperm and other biological materials has been of great interest to industry and academia. U.S. Pat. Nos. 7,526,116 and 7,720,272 disclose a system for automated identification of a sperm in an area of interest on a microscope slide. U.S. Pat. No. 7,252,642 and US Pat. Appl. Publ. Nos. 2011149287, 2011147591, 2007245812 and 20040146848 disclose a method for quantifying the total sperm concentration in a sample, a video visualization system, and a displaying means for viewing sperm samples. U.S. Pat. No. 7,521,696 discloses a method for analyzing fluorescently labeled biological material. A user uses fluorescence in images to manually track the biological material. U.S. Pat. Nos. 7,042,639, 7,106,502 and 7,268,939 disclose an imaging system that utilizes image processing techniques to identify, detect, and track microscope specimens, such as biological cells. US Pat. Appl. Publ. No. 2010046823 discloses an automated system and method for visually tracking moving objects (e.g., biological cells).

U.S. Pat. Nos. 4,402,614 and 4,176,953 disclose a method that directs a beam of light at sperm, and measures the reflections of light from the sperm per unit time to measure sperm motility. U.S. Pat. No. 7,838,210 discloses a method for sorting sperm cells. U.S. Pat. Nos. 7,943,384, 7,758,811, and 7,799,569 disclose a system for sorting and classifying sperm cells based on certain characteristics of the sperm such as DNA content. U.S. Pat. No. 4,896,967 and U.S. Pat. No. 4,896,966 disclose an optical system that uses a radiation sensing means and signal processing to extrapolate the motion of sperm cells, bacteria, and particles. U.S. Pat. No. 7,855,078 discloses a flow cytometer that is able to separate sperm based on one or more characteristics. US Pat. Publication No. 2011061472 discloses microfluidic devices for separating sperm and for determining sperm quality of a semen sample.

Several algorithms have been developed in the field of computer-assisted sperm analysis (CASA) to track sperm trajectories, measure sperm velocity, and evaluate sperm energetic (L. Shi, J. Nascimento, C. Chandsawangbhuwana, E. Botvinick, and M. Berns, "An automatic system to study sperm motility and energetics," *Biomed. Microdevices*, vol. 10, pp. 573-583, 2008; L. Z. Shi, J. M. Nascimento, M. W. Berns, and E. L. Botvinick, "Computer-based tracking of single sperm," *J. Biomed. Opt.*, vol. 11, 2006; M. Berezansky, H. Greenspan, D. Cohen-Or, and O. Eitan, "Segmentation and tracking of human sperm cells using spatiotemporal representation and clustering," *Progr. Biomed. Opt. Imaging Proc.*, vol. 6512, 2007; H. Oku, M. Ishikawa, N. Ogawa, K. Shiba, and M. Yoshida, "How to track spermatozoa using high-speed visual feedback," in *Proc. Annu. Int. Conf. IEEE Eng. Med. Biol. Soc. EMBC,* 2008, pp. 125-128; and R. P. Amann and D. F. Katz, "Reflections on CASA after 25 years," *J. Androl.*, vol. 25, pp. 317-325, 2004).

The aforementioned computer assisted sperm analysis methods, however, are only concerned with visual sperm analysis, and do not enable automated sperm manipulation. In view of the foregoing, what is needed is a system and methods for performing automated sperm manipulation. Automated sperm manipulation overcomes the limitations inherent in manual sperm manipulation. To achieve automated sperm manipulation the following may be required: (1) a system integrating multiple motorized positioning devices and imaging devices; (2) computer vision algorithms for tracking the spatial location of the sperm in real time; and (3) motion control methods for controlling the motorized positioners to manipulate sperm.

Holding pipettes are standard tools used in ICSI for immobilizing a single oocyte. Searching for an oocyte and immobilizing it are time consuming. What is also needed is a device, preferably a disposable device, for immobilizing multiple oocytes and for containing sperm on the same device to significantly facilitate ICSI.

There are several existing patents on vacuum-based cell holding devices. US Pat. Appl. Publ. No. 2007048857 and EPO Pat. Publ. No. 1752221 disclose a cell trapping plate with application of negative pressure suction through trapping holes. Similarly, U.S. Pat. Appl. Publ. No. 20050250197 and U.S. Pat. No. 5,262,128 also disclose cell trapping devices via through-holes and vacuum application. The through holes of the devices of these patent documents are on the device surface.

There are no cell holding devices which are capable of immobilizing multiple oocytes and containing sperm on the same device for ICSI use. What is needed is a device design that is (1) able to effectively trap/release multiple oocytes and hold sperm; (2) able to properly contain cells and liquid medium on the device; and (3) disposable and low cost.

SUMMARY OF THE INVENTION

In one embodiment the present invention provides for a system for automated tracking and manipulation of a motile specimen under a microscope characterized in that said system comprises: (a) a first positioner, said first positioner adapted for supporting a substrate having the motile specimen, and for controlling the motion of said substrate, said first positioner being operationally linked to a host computer; (b) a second positioner to control motion of a manipulating means for manipulating the motile specimen in the substrate, said second positioner being operationally linked to the host computer; (c) a microscope means for viewing the motile specimen in the substrate and the manipulating means, said microscope means being operationally linked to the host computer; (d) an image acquiring unit capable of being mounted on the microscope means, said image acquiring unit being operationally linked to the host computer, and said image acquiring unit capable of providing images to the host computer of the motile specimen and the manipulating means; and (e) the host computer, said host computer including means for processing the images provided by the image acquiring unit, means for motion control of the first positioner for automatically tracking the motile specimen, and means for motion control of the second positioner for automatically manipulating the motile specimen with the manipulating means.

In another embodiment the present invention provides for a method of automatically manipulating a motile specimen under a microscope characterized in that said method comprises the following steps: (a) placing a substrate having the motile specimen on a first positioner mounted to a microscope means having an image acquiring unit; (b) acquiring microscopic images of the motile specimen and a micropipette means used to manipulate the motile specimen with the image acquiring unit; (c) automatically tracking the motile specimen on the substrate based on the images of the motile specimen and micropipette means using the first positioner; (d) automatically moving the micropipette means using a second positioner connected to the micropipette means to a location substantially proximal to the motile specimen; and (e) automatically immobilizing the motile specimen using the micropipette means for manipulation of the motile specimen.

In aspects of the invention the motile specimen includes sperm.

A device for holding motile cells and non-motile cells is also disclosed. As such, in another embodiment the present invention provides for a device for holding motile cells and non-motile cells, said device comprising: (a) one or more wells capable of receiving the motile cells; (b) a sealed chamber having an air outlet; and (c) one or more wells capable of receiving the non-motile cells, each of the one or more wells for non-motile cells including an array of through holes operable for holding the non-motile cells, each through hole in the array having openings on opposing ends, said through holes connecting the well for non-motile cells to the sealed chamber.

In another embodiment, the present invention provides for a device for holding motile cells and non-motile cells, said device comprising: (a) a first means having a top surface and a bottom surface, the top surface having at least one well for non-motile cells, the at least one well for non-motile cells including an array of through holes for holding the non-motile cells, each through hole in the array extending from the top surface to the bottom surface; and (b) a second means connected to the bottom surface, the second means having at least one well for motile cells and an area configured for defining a chamber below the well between the bottom surface and the such that the through holes in the array connect the chamber with the well for the non-motile cells, the chamber having an air outlet.

In aspects of the invention the motile cells are sperms and the non-motile cells are oocytes.

BRIEF DESCRIPTION OF DRAWINGS

A brief description of one or more embodiments is provided herein by way of example only and with reference to the following drawings, in which.

DETAILED DESCRIPTION OF THE INVENTION

1. Definitions

"Automatic/automated" as used in this document means that manipulation of motile specimen is free of human operator control (for example manual and/or joy-stick based control) or where human intervention is limited to entering input data. Software (image processing and motion control) and hardware are integrated in a computer machine to reduce or eliminate the operator's intervention.

"Control software/algorithms" as used in this document means motion control laws (e.g., proportional-integral-derivative) implemented in the form of computer program that automates tracking and manipulation of motile specimen with the system and methods presented in this invention.

"Image processing" as used in this document means control software capable of extracting, analyzing and applying the data or information from images taken by an image acquiring unit, camera/microscope in real time, and hence automatically identifying and tracking the motile specimen and micropipette with the system and methods presented in the invention.

"Manipulation" as used in this document means the immobilization, aspiration and/or dispensation of motile specimen, such as sperm or any other unicellular or multicellular microbiological entities.

"Motorized" as used in this document means that positioning devices are equipped with a motor or motors which are controlled via control algorithms and strategies.

"Motion control" as used in this document means computer control of the motions of the positioning devices (motorized stage, micromanipulator, and motorized pressure unit) to perform manipulation of motile specimen with the hardware and methods presented in this invention.

The present invention discloses a system and methods for automated manipulation of motile specimen. The present invention also provides for a device for holding motile specimen such as motile cells and non-motile cells.

2. System for Automated Tracking and Manipulation of Motile Specimen

Figure 1:
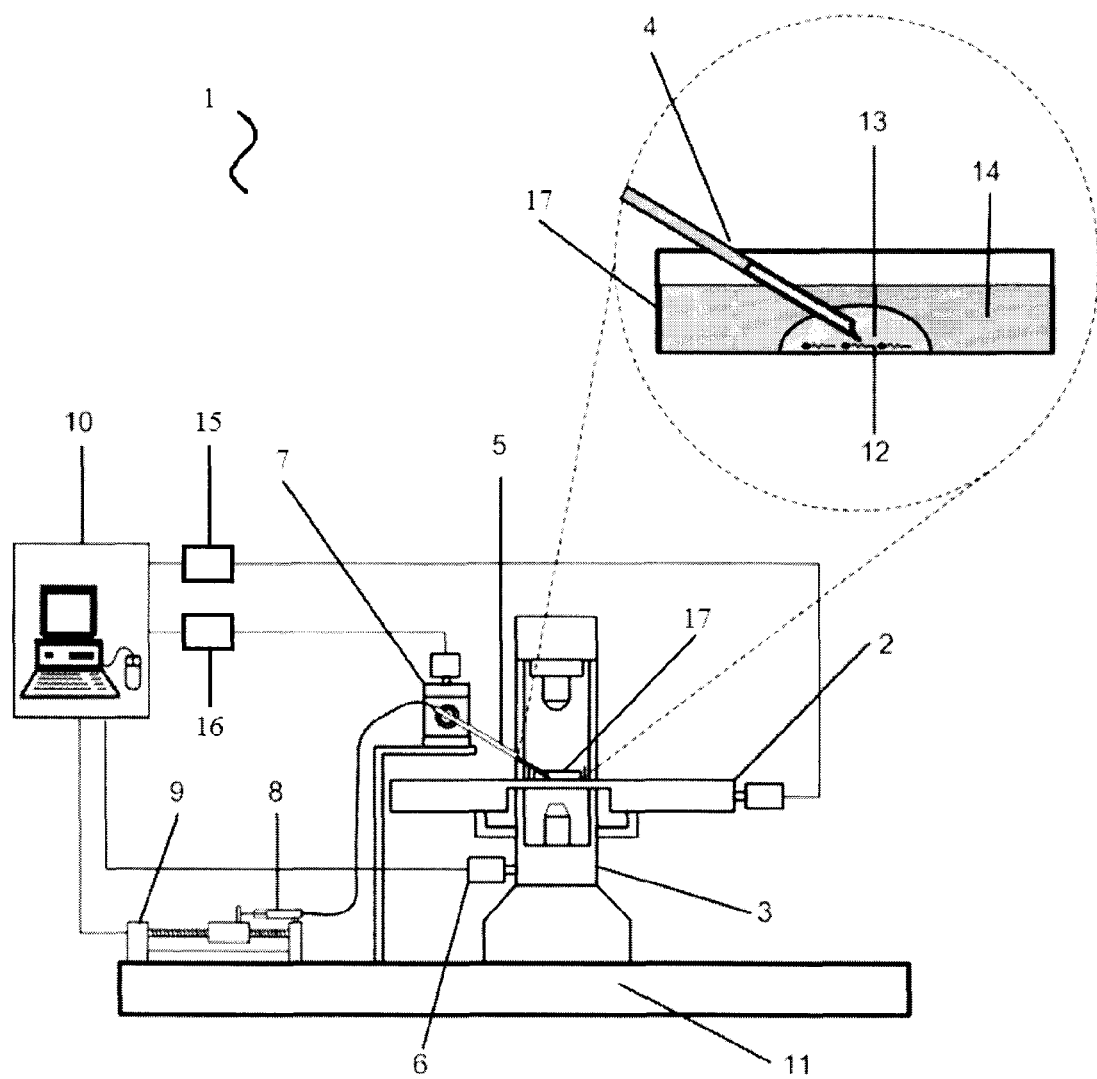
FIG. 1 illustrates the schematic view of an automated sperm manipulation system in accordance to one embodiment of the present invention.

A schematic view of the system for automated tracking and manipulation of motile specimen in accordance to one embodiment of the present invention is shown in FIG. 1.

According to this embodiment, a system 1 for automated tracking and manipulation of motile specimen may include the following components:

(i) a host computer 10 which may include control software/algorithms for motion control and image processing;

(ii) a microscope 3, such as an inverted optical microscope;

(iii) an image acquiring unit such as a camera 6, which may be mounted on the microscope 3; and (iv) at least two motorized positioning devices ("positioners") 2, 7, such as a multi-degrees-of-freedom motorized stage 2 or a multi-degrees-of-freedom motorized microrobot/micromanipulator 7 which may be capable of controlling the motion of a substrate 17 used for holding the motile specimen such as sperm 12, and manipulation tools such as a micropipette 4 for manipulating motile specimen respectively; and (v) at least two positioner control devices 15, 16 connected to or mounted on the host computer 10 for delivering control signals to the two positioners 2, 7 for computer-controlled motion control of the two positioners.

The system 1 may also include a motorized pressure unit for motile specimen aspiration and dispensation. The motorized pressure unit may include a syringe 8 and a motorized stage 9.

The system may also include a substrate, such as a holding device or container 17 for holding or containing the sperm 12.

The system may also include a vibration isolation table 11 to minimize vibration of the microscope, image acquiring unit and the positioning devices.

The motorized positioning devices 2, 7, microscope 3, image acquiring unit 6, pressure unit 8, 9 may be controlled by the host computer 10 so as to automate manipulation of the motile specimen.

Although this particular configuration of the system of the present invention may be used for tracking and manipulation of sperm, it should be expressly understood that this is an illustrative example only and that the present invention is readily adaptable for the tracking and manipulation of any other motile specimen having or not having a tail portion. Other motile specimen may include unicellular or multicellular microbiological entities.

With reference to FIG. 1, the substrate 17 containing sperm and sperm culture medium may be placed on the multi-degrees-of-freedom motorized stage 2, which may be mounted on the microscope 3. A micropipette 4, which may be a straight or angled micropipette (glass capillary) may be connected to a micropipette holder 5 to manipulate the sperm 12. A camera 6 may be installed on the microscope 3 to provide the system with microscopic images of the sperm 12 and micropipette 4. Multiple motorized positioning devices, such as a multi-degrees-of-freedom motorized stages or micromanipulators may be used to perform procedures in automated sperm manipulation. The multi-degrees-of-freedom motorized stage 2 may be used to move the substrate 1, so that the sperm may appear in the field of view of the microscope 3. The multi-degrees-of-freedom motorized micromanipulator 7 may be used to control the motion of the micropipette 4. The motorized pressure unit may be used for sperm aspiration and dispensation. A syringe 8 which may be included in the pressure unit may be connected to the micropipette 4. A one-degree-of-freedom motorized unit 9 may serve to control the piston inside the syringe 8 to adjust the pressure inside the micropipette 4. The host computer 10 may be used to automatically control the multiple motorized positioning devices 2, 7, 9 and to automatically process images from the microscope 3 and camera 6.

3. Method for Automated Tracking and Manipulation of Motile Specimen

In one embodiment the present invention provides for a method of automatically tracking and manipulating a motile specimen. A method of automatically tracking and manipulating a motile specimen may start by placing a substrate having the motile specimen on a first positioner capable of moving the substrate such that the motile specimen may appear in the field of view of a microscope having an image acquiring unit. The first positioner, microscope means and image acquiring unit may be linked to a host computer. The host computer may include control software for motion control and image processing. Microscopic images of the motile specimen and a micropipette used to manipulate the motile specimen may be automatically obtained with the image acquiring unit. Based on the information included in the microscopic images, the host computer may automatically track the motile specimen on the substrate using the first positioner. Using the tracking information, the micropipette may be automatically moved using a second positioner connected to the micropipette to a location substantially proximal to the motile specimen and the motile specimen may be substantially immobilized using the micropipette for manipulation of the target motile specimen.

Although the methods presented herein below may relate to the automatic tracking and manipulation of sperm, it should be expressly understood that this is an illustrative example only and that the present invention is readily adaptable for the tracking and manipulation of any other motile specimen having or not having a tail portion. Other motile specimen may include unicellular or multicellular microbiological entities.

Figure 2:
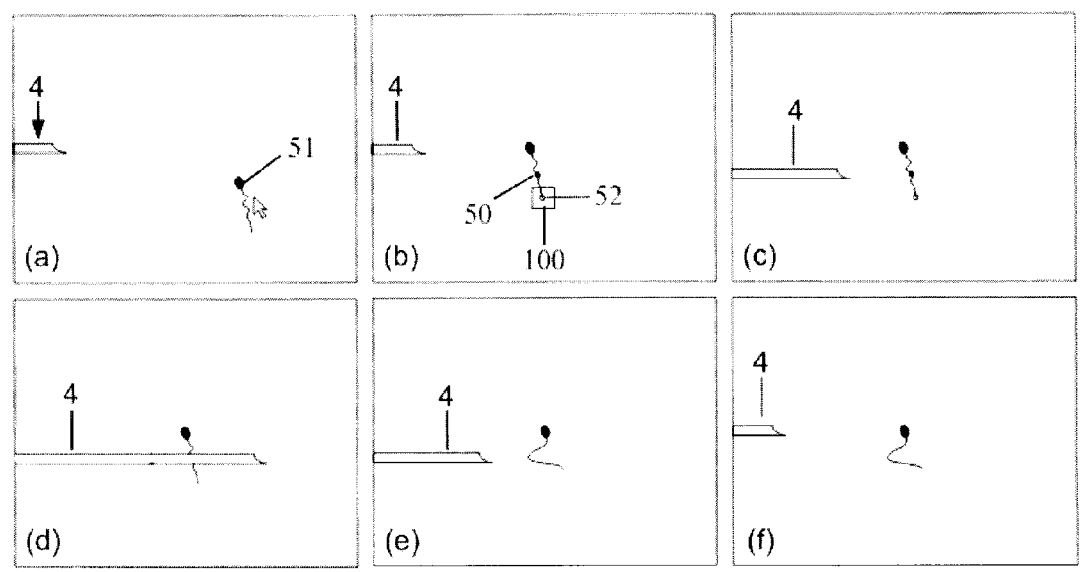
FIG. 2 illustrates a sperm immobilization operation sequence in accordance to one embodiment of the present invention.

The sequence of automated sperm selection and immobilization method in accordance to one embodiment of the present invention is shown in FIG. 2. FIG. 2 illustrates the selection and immobilization of one sperm cell; however it should be understood that the method may be used to select and immobilize more than one sperm cell. The sequence may start by selecting one sperm cell. The sperm selection step shown in FIG. 2(a) may be manual or automated. A human operator may first select a sperm of interest or target sperm by computer mouse clicking on or in proximity to the head 51 of the sperm, as illustrated in FIG. 2(a). This step may permit the human operator to select a desired sperm based on sperm morphology and motility, thus exercising his/her expert knowledge. Alternatively, the selection of a target sperm may also be automated via image processing without a human operator. The sperm head 51 may then be tracked to provide visual feedback of the sperm position for every consecutive image captured by the image acquiring unit included in the system of the present invention. The spatial distance from the sperm head 51 to the center of the field of view of the camera may be determined. This spatial distance may be input into a controller, and it may be used by the host computer of the system of the present invention to control the multi-degrees-of-freedom motorized stage to adjust the spatial distance to zero, so that the sperm may be kept at the center of the field of view, as shown in FIG. 2(b). The distance calculation and motion of the multi-degrees-of-freedom motorized stage may be automatically performed by the system of the present invention for every consecutive image captured by the camera to maintain the sperm at the center of the field of view.

In one embodiment of the present invention, a sperm tail tracking algorithm may be used to locate the tail 52 position of a sperm in each frame of image. The area in which the sperm tail is located or approximately located (herein termed 'tail region') and indicated by a box 100 in FIG. 2(b), may be computed by adding a scaled value of sperm's average direction of movement to each spatial component of the sperm head position 51. The sperm's average direction of movement may be found by averaging a number of the most recent sperm direction of movement values. For example, the sperm's average direction of movement may be found by averaging about 30 of the most recent sperm direction of movement values. A person of ordinary skill in the art would understand that less than 30 sperm direction of movement values or more than 30 sperm direction of movement values may also be used to obtain the sperm's average direction of movement. The number of direction of movement values used may range from 15 to 60 depending on the camera capturing frame rate and the host computer's computational ability to process images in real time. The sperm direction of movement in a given image frame may be computed by subtracting the sperm head position in the previous image frame from the sperm head position in the given image frame. The sperm's average direction of movement may be used to avoid errors caused by abrupt local changes in the sperm's direction of movement between consecutive images taken by the camera (i.e. image frames). The sperm tail tracking algorithm may then be able to verify that a tail is present in the tail region by extracting the feature of flicker from the image in the tail region. Flicker feature may, for example, be computed by first taking the absolute difference between six consecutive tail region image frames. The resulting images from the aforementioned subtraction operation may be grayscale images. These grayscale images may then be added together to form the flicker feature image for the tail region. Pixel values in the flicker feature image greater than 0 (non-black pixels) represent areas of temporal change (e.g., the moving sperm tail). Areas of high intensity (i.e., areas much greater than 0 in pixel values) in the flicker feature image correspond to areas of greater temporal change. In contrast, pixel values of 0 (black pixels) in the flicker feature image represent no significant temporal change (e.g., an unchanging background). By using previous tail region image frames, the flicker feature image represents a history of the tail's positions in the previous and current image frames. A person of ordinary skill in the art would understand that less than 6 consecutive tail region image frames or more than 6 consecutive tail region image frames may be used to extract flicker. The number of consecutive tail region image frames used for creating the flicker feature image may range from 2 frames to 30 frames. A minimum of 2 frames may be required to perform the absolute subtraction operation for flicker feature computation. If the pixel sum of the flicker feature image is above a specific threshold, a tail may be considered to be present, otherwise the tail may be considered to be lost or not present. The threshold value may be found experimentally by comparing the pixel sum values of images of the tail region where a tail is present against cases where the tail is absent. Once the sperm tail is confirmed to exist within the tail region area, the sperm tail tracking algorithm may then find a position on the sperm tail. A relative position on the sperm tail may be obtained by finding the area in the flicker image of the tail region with the highest pixel intensity value. The sperm head 51 and tail 52 positions may then be averaged to locate the midpoint position 50 of the sperm tail for sperm tail immobilization, as shown in FIG. 2(b).

The micromanipulator of the system of the present invention for controlling the micropipette 4 may then undergo a sequence of motions to move the micropipette 4 to tap/slash/crimp the midpoint position 50 of the sperm to immobilize the sperm. As shown in FIG. 2(c) using the micromanipulator (not shown in FIG. 2), the micropipette 4 may be automatically moved towards the midpoint position 50 of the sperm tail. The micropipette 4 may then press the sperm tail against the bottom surface of the container (e.g., petri dish) as illustrated in FIG. 2(*d*). The micropipette 4 may then roll over the sperm tail for immobilization of the sperm against the bottom surface as illustrated in FIG. 2(*e*). Finally, the micropipette 4 may be brought back to the left of the field of view, ready for a next sperm immobilization operation, as shown in FIG. 2(*f*).

It should be understood that the aforementioned tail tracking algorithm is only one example for locating a position on the sperm for immobilization. Other visual information, such as sperm direction of movement, sperm speed and sperm angular velocity may be used to locate a position on or within the proximity to the sperm for performing immobilization.

Figure 3:
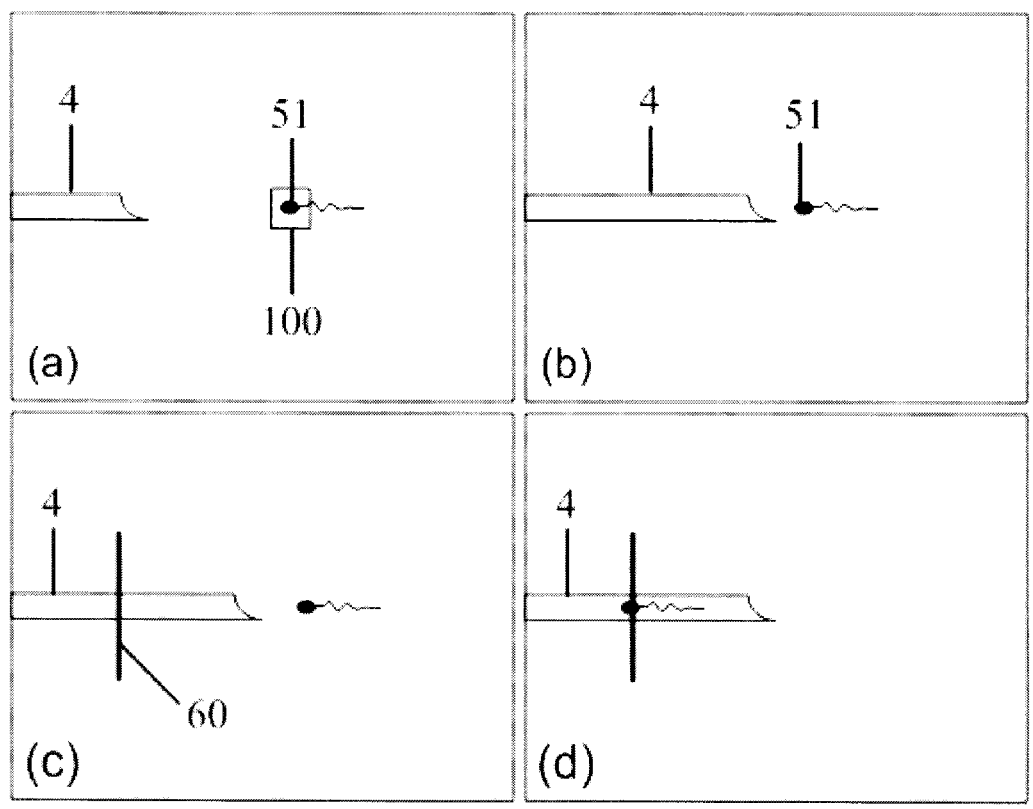
FIG. 3 illustrates a sperm aspiration operation sequence in accordance to one embodiment of the present invention.

The operation sequence of sperm aspiration method is shown in FIG. 3. Sperm aspiration may start by tracking the sperm head 51 using the same image processing method that may be used in automated sperm immobilization, as shown in FIG. 3(*a*). The tip of the micropipette 4 may be automatically identified using image processing. The spatial distance between the micropipette tip and the sperm head may be computed. The micromanipulator may then move the micropipette 4 automatically to be within proximity to the sperm head position 51 via motion control, as shown in FIG. 3(*b*).

Figure 4:
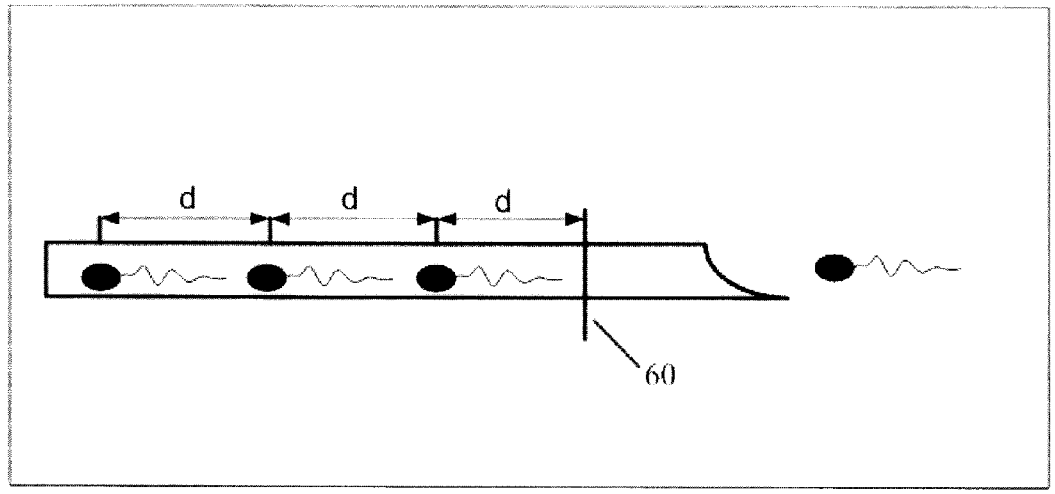
FIG. 4 illustrates a scenario of multiple sperm aspirated and positioned inside a micropipette in accordance to one embodiment of the present invention.

A human operator may then input (e.g. via computer mouse click) the desired destination position 60 in the micropipette 4 for the sperm to reach, as shown in FIG. 3(*c*). Alternatively, the desired position 60 may be defined automatically via image processing without human input. The motorized pressure unit of the system of the present invention may then be automatically controlled to aspirate the sperm into the micropipette. The spatial distance between the specified destination and the tracked sperm head 51 may be input into a controller, which may be used by the system of the present invention to control the motorized pressure unit to move the sperm to the designated destination within the micropipette, as shown in FIG. 3(*d*). The sperm aspiration method may also be applied to aspirate multiple sperm. Multiple sperm may be aspirated into the micropipette and positioned with constant space (distance d) between two sperm, as shown in FIG. 4. By loading multiple sperm cells, the system does not need to go back to the sperm pool for injecting multiple oocytes.

Figure 5:
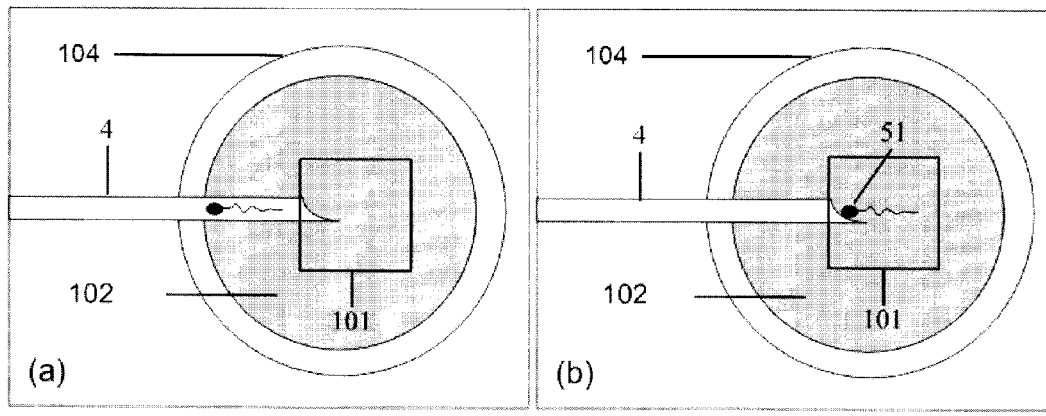
FIG. 5 illustrates a sperm dispensation operation sequence in accordance to one embodiment of the present invention.

The operation sequence of the automated sperm dispensation method is shown in FIG. 5. FIG. 5 shows a scenario in which one sperm may be dispensed into the cytoplasm 102 of an egg 104 in the Intracytoplasmic Sperm Injection (ICSI) process. An area 101 within the proximity to the tip of the micropipette 4 may be set (either automatically or by the user via mouse click) and the image of this area may be recorded first, as shown in FIG. 5(*a*). The automated system of the present invention may control the motorized pressure unit to dispense the sperm out of the micropipette 4 with a fine controlled pressure. When the sperm head 51 comes out of the micropipette 4 and appears inside the area 101, the sperm head 51 may be detected visually either by a human or automatically via instructions provided by the image processor in the host computer, as shown in FIG. 5(*b*). The system may then stop the motorized pressure unit.

Figure 6:
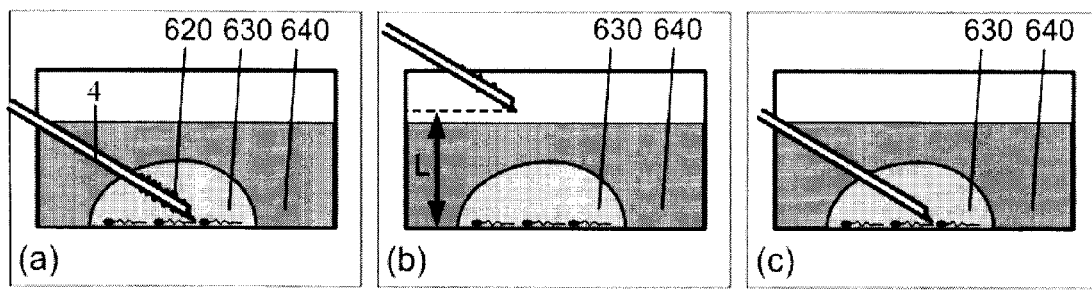
FIG. 6 illustrates an operation sequence of cleaning debris adhered to the outside of a micropipette in accordance to one embodiment of the present invention.

In ICSI, a sperm sample together with culture medium may be placed in a substrate (e.g., petri dish). Mineral oil may then be added to cover the medium and sperm. During sperm manipulation, debris around the micropipette may easily adhere to the outside surface of the micropipette or clog the inside of the micropipette. Therefore, it may be necessary to clean the micropipette regularly to reduce the adverse effects caused by the debris. FIG. 6 shows the operation sequences which may be used to clean debris 620 adhered to the outside of the micropipette 4. The micropipette 4 may be raised (by distance L) into the air by the micromanipulator, as shown in FIG. 6(*b*), and lowered to its original position automatically. Most debris 620 may be removed by the surface tension of the mineral oil 640 when the micropipette 4 passes through the air-mineral oil interface.

Figure 7:
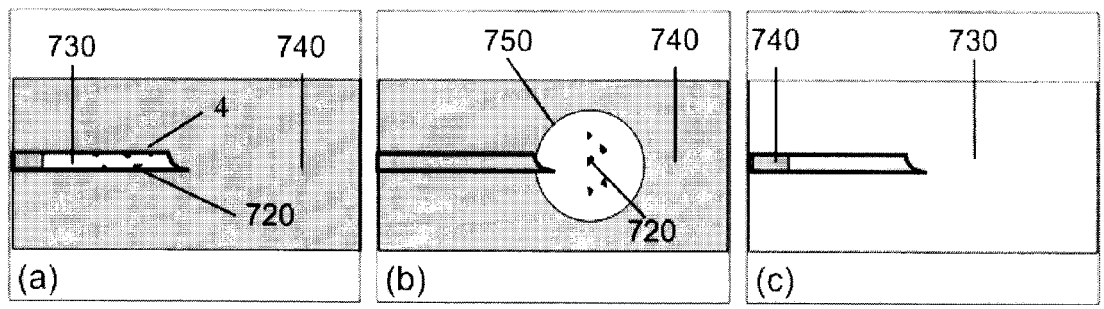
FIG. 7 illustrates an operation sequence of cleaning clog inside of a micropipette in accordance to one embodiment of the present invention.

The operation sequence of cleaning clogging debris 720 inside the micropipette is shown in FIG. 7. The micropipette 4 may first be moved into the mineral oil 740 by the micromanipulator, as shown in FIG. 7(*a*). Then a pressure impulse may be provided by the motorized pressure unit of the system of the present invention to push a certain amount of the sperm culture medium out of the micropipette 4, as shown in FIG. 7(*b*). A culture medium bubble 750 may be generated at the tip of the micropipette 4. Most clogging debris 720 inside the micropipette may be expelled into the bubble 750. The micropipette 4 may then be submerged back into the culture medium 730 and aspirate a certain amount of the culture medium, as shown in FIG. 7(*c*).

It should be understood that any culture medium known in the art for maintaining sperm may be used in the system and methods of the present invention. In one aspect, the culture medium may be any viscous medium known in the art that may serve to slow the mobility of sperm and facility sperm tracking and immobilization (see for example J Assist Reprod Genet. 2010 January; 27(1): 13-16).

4. Device for Motile Cells and Non-Motile Cells

In one embodiment the present invention relates to a device for holding motile cells and non-motile cells. The device of the present invention may include at least one well for the motile cells, and at least one well for non-motile cells. The at least one well for non-motile cells may include an array of through holes for substantially holding the non-motile cells, each through hole in the array may have openings on opposing ends. The through holes may connect the well for non-motile cells to a sealed chamber. The sealed chamber may include an air outlet.

Although the examples provided herein relate to the use of the devices of the present invention in Intracytoplasmic Sperm Injection (ICSI), it should be expressly understood that this is an illustrative example only and that the present invention may be readily adaptable for other cell manipulation procedures.

This invention discloses the first disposable device capable of batch hold/release oocytes and sperm for ICSI use.

Figure 8:
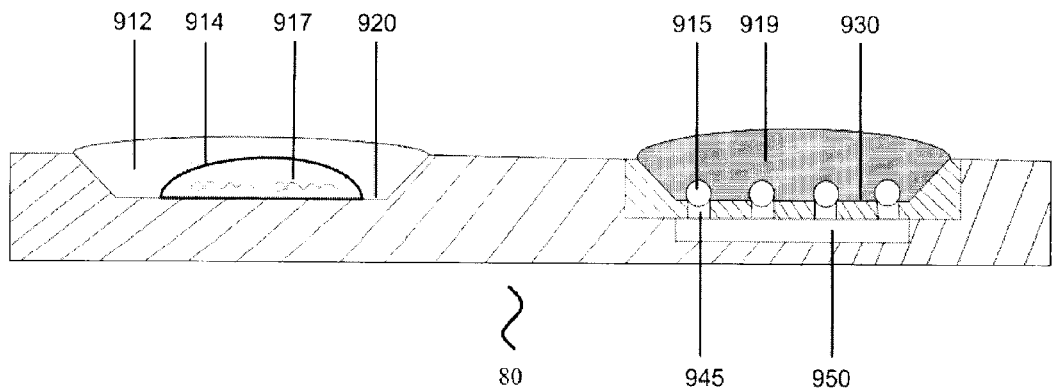
FIG. 8 illustrates a side sectional view of a device for holding sperm and immobilize/release oocytes in accordance to one embodiment of the present invention.

With reference to FIG. 8, a device 80 according to one embodiment of this invention may include a sperm well or reservoir 920 and an oocyte well 930. The device 80 may also include a sealed chamber 950 in fluid communication with the oocyte well 930. Sperm well 920 may be capable for receiving sperm 917 and culture medium 914 for the sperm. Mineral oil 912 may be added to cover the medium 914. The sperm well 920 may be designed to prevent the overflow of the mineral oil 912.

With continued reference to FIG. 8, the oocyte well 930 may be capable of receiving oocyte culture medium 919. After the oocytes 915 are transferred into the oocyte well 930, a low negative pressure may be applied through the sealed chamber 950. Each oocyte 915 may be substantially immobilized on top of a through-hole 945 which may be designed to connect oocyte well 930 to the sealed chamber 950, such that the sealed chamber 950 and the oocyte well 930 may be in fluid communication. The device 80 may then be transferred to the stage of an inverted microscope for ICSI operation. After all the oocytes 915 are injected with sperm 917, a low positive pressure may be applied via the sealed chamber 950, and the oocytes 915 may be released from the through-hole 945 for collection.

In one embodiment, the device of the present invention may be constructed as structure having two or more parts. The two or more parts may be configured such that they may be assembled into the device. In one embodiment, the device may be constructed as a structure having two parts: an upper or top part and a base part.

Figure 9:
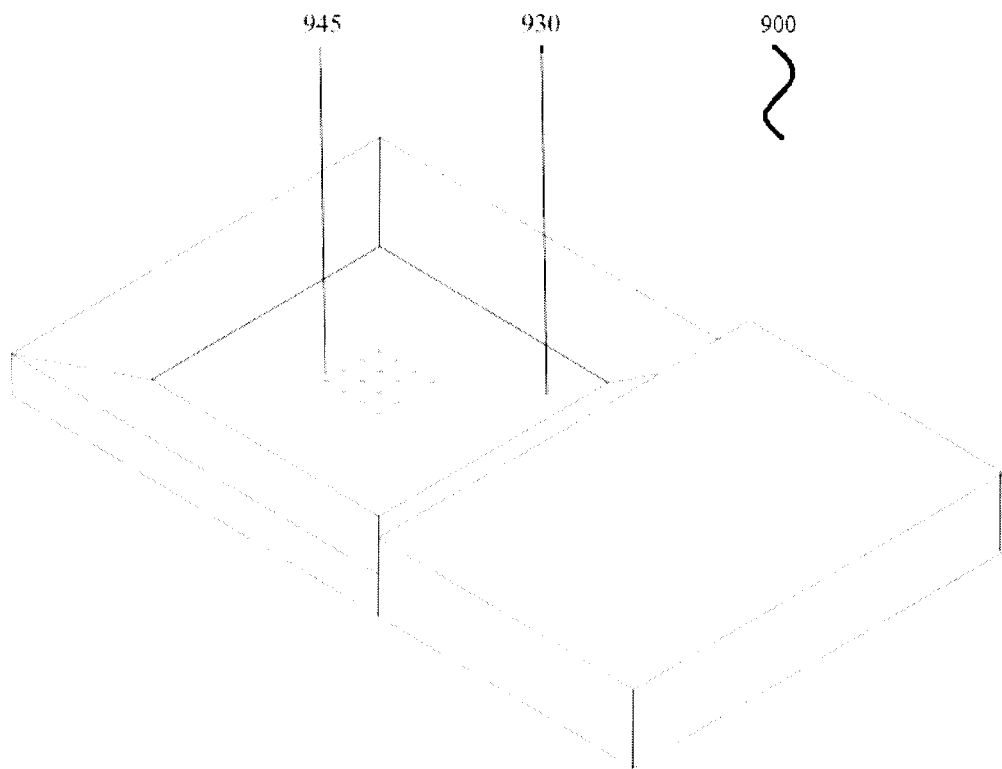
FIG. 9 shows a perspective view of the top part of a device for holding sperm and immobilize/release oocytes in accordance to one embodiment of the present invention.

With reference to FIG. 9, the upper or top part 900 of the device of the present invention may include the oocyte reservoir 930 and an array of through-holes 945 inside the reservoir 930.

Figure 10:
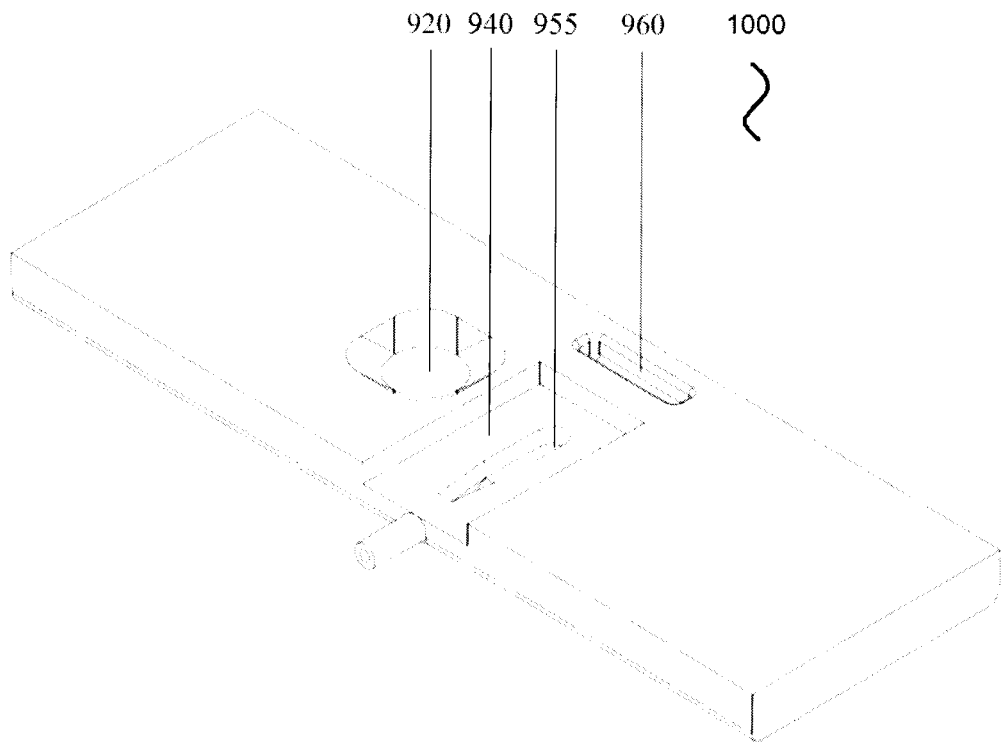
FIG. 10 shows a perspective view of the base part of a device for holding sperm and immobilize/release oocytes in accordance to one embodiment of the present invention.
Figure 11:
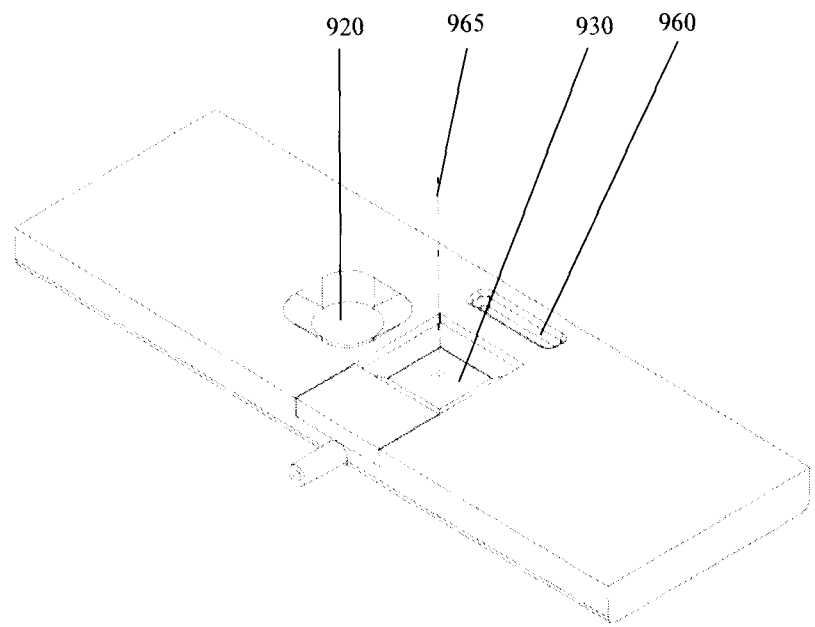
FIG. 11 illustrates the assembly of the base part and the top part of a device for holding sperm and immobilize/release oocytes in accordance to one embodiment of the present invention.

With reference to FIG. 10, the bottom or base part 1000 of the device of the present invention may include the sperm reservoir 920, a depression 940 having a channel 955, and the connector or air outlet for connecting the channel 955 to a pressure control device (not shown). The depression 940 may be configured for receiving the top part of the device of the present invention. The channel 955 may be sealed after the top part and the base part are coupled thereby forming the sealed chamber of the device. The complete device assembly is shown in FIG. 11. A pouring gate 960 may also be provided as a feature for facilitating manufacturing, such as using injection molding.

It should be understood that other designs of the parts of the device may be possible. For example, the wells capable of receiving the non-motile cells may be molded on the top part. The air outlet may be molded into a separate part. Therefore, the position of each functional part and the number of molded parts may vary. As such, in one embodiment, the device of the present invention may be an assembly having at least two parts, one part including the one or more wells capable of receiving the non-motile cells, and one part including the one or more wells capable of receiving the motile cells.

During procedures such as ICSI, proper orientation of the polar body of the oocyte may be required to avoid the penetration of the oocyte's polar body. When an oocyte is rotated, translational motions during rotation may cause the oocyte to change its position in the image plane or escape out of the field of view of the microscope. In order to minimize the translational motions, according to one embodiment of the present invention, the center of the oocyte well may be designed to be coincident along the rotational axis of the device 965, as shown in FIG. 11.

Figure 12:
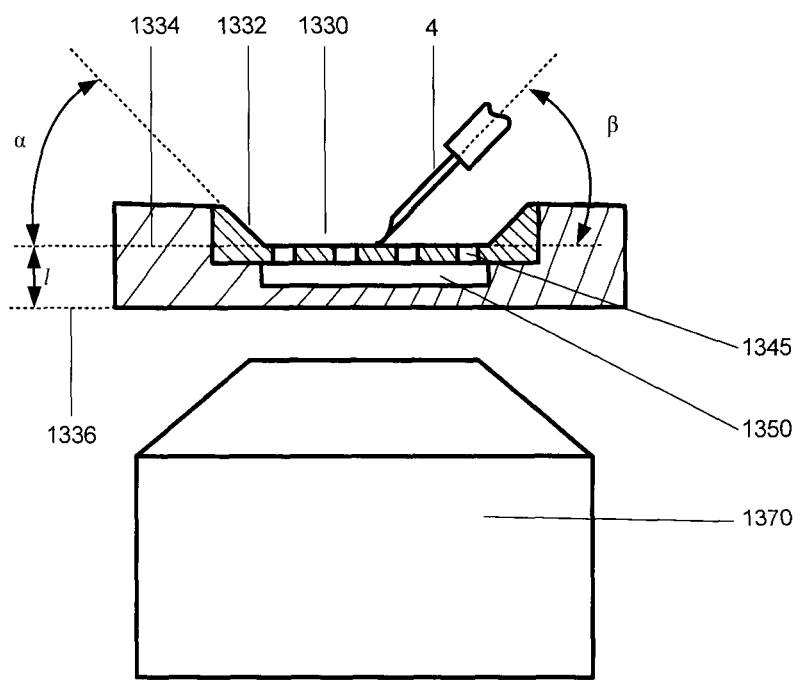
FIG. 12 illustrates a side sectional view of a device for holding sperm and immobilize/release oocytes in accordance to one embodiment of the present invention during ICSI operation.

The side cross sectional view of the oocyte well area is shown in FIG. 12. The walls 1332 of the oocyte reservoir 1330 may be designed to be sloped with a certain angle α. The slope angle α may be smaller than the injection micropipette 4 bent angle β, so that the motion of the injection micropipette 4 may not be interfered/contacted by the walls 1332 of the oocyte well 1330 during injection. The depth of the oocyte well 1330 may be designed to be deep enough to contain culture medium for fully covering the oocytes.

ICSI is commonly performed on inverted microscopes. With reference to FIG. 12, the distance from the bottom 1334 of the oocyte well 1330 to the bottom 1336 of the device may be designed to be within the working distance of the objectives 1370 on the inverted microscope. The through-hole array 1345 on the bottom of the oocyte well may be connected to a sealed chamber 1350. When negative/positive pressure is applied to the sealed chamber 1350, oocytes are held on/released from the through-hole array 1345 in a batch manner.

Figure 13:
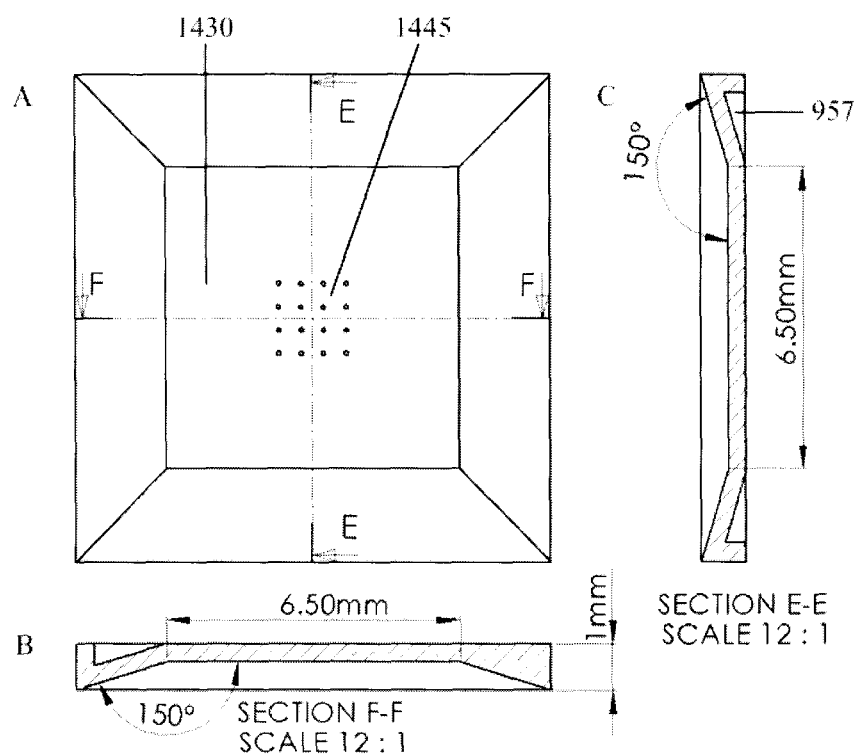
FIG. 13A illustrates a top view of the structure of through-hole array of a device for holding sperm and immobilize/release oocytes in accordance to one embodiment of the present invention.
FIG. 13B illustrates a side sectional view of the structure illustrated in FIG. 13A through Section F-F.
FIG. 13C illustrates a side sectional view of the structure illustrated in FIG. 13A through Section E-E.

One possible design of through-hole array is shown in FIGS. 13A and 13B. The number of through-holes in an array may vary, depending on the number of oocytes to inject with sperm. The number of oocytes for ICSI varies among patients from superovulation although it is within a limited range. The pattern of through-hole array may play an important role to facilitate oocytes self-distribution under negative pressure and affects injection efficiency. The through holes may be arranged in a substantially square or substantially rectangular pattern area 1445. The center of the pattern 1445 may be located at the center of the bottom of the oocyte well 1430. The pattern area 1445 may be sized so that when the oocytes are transferred to the area, the oocytes may be sucked to a through hole with minimal travel. The pitch between two through holes may be sufficient to prevent the injection micropipette from touching adjacent oocytes during injection. For mammalian oocytes, a pitch of about 0.4 mm may appropriate. The diameter of through holes may be designed to substantially hold oocytes during injection, while preventing the deformation of oocytes. The proper diameter of the through holes may be from about 30 microns to about 40 microns for mouse oocytes, about 35 microns to about 45 microns for hamster oocytes, and about 45 microns to about 55 microns for human oocytes.

With reference to FIG. 13C, a cavity 957 may be opened up around the perimeter of the oocyte well on the bottom surface, so that it may be feasible to build the oocyte bottom as thin and flat as possible with injection molding. The contact area surrounding the chamber zone between the top part and the base part may be kept large enough to guarantee easy and reliable bonding. The location of the through holes may be arranged so that the through holes may be within the chamber zone in alignment.

Figure 14:
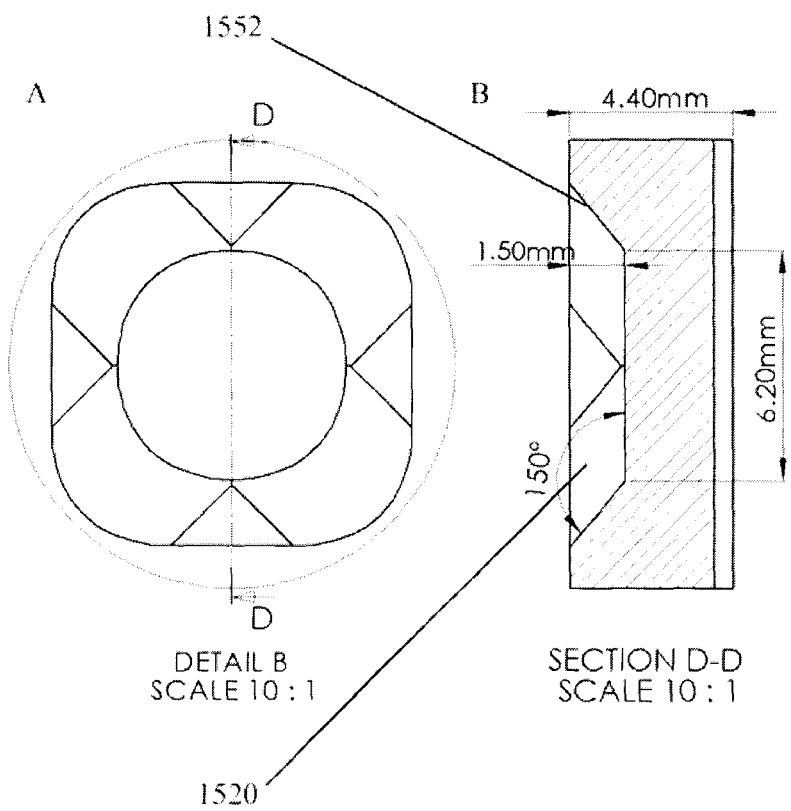
FIG. 14A illustrates a top view of a design of a sperm well of a device for holding sperm and immobilize/release oocytes in accordance to one embodiment of the present invention.
FIG. 14B illustrates a side sectional view of the sperm well illustrated in FIG. 14A through Section D-D.

In one embodiment, the position of the sperm well in the device of the present invention may be designed to be relatively close to the oocyte well, as shown in FIG. 11. A side sectional view through section D-D of FIG. 14A of sperm well 1520 of the device of the present invention is shown in FIG. 14B. Similar to the oocyte well, the walls 1522 of the sperm well 1520 may be designed to be sloped with certain angle α. The slope angle α may be smaller than the micropipette bent angle β, so that the injection micropipette may not interfere with/touch the walls of the sperm well during sperm tapping and aspiration. The depth of the sperm well 1520 is designed to be deep enough to contain sufficient culture or other medium and mineral oil. In order to obtain clear microscopy focus on sperm, the distance from the bottom of the sperm well to the bottom of the device may be designed to be within the working distance of the objectives on the inverted microscope. The bottom surface of the sperm well may be flat without features.

Figure 15:
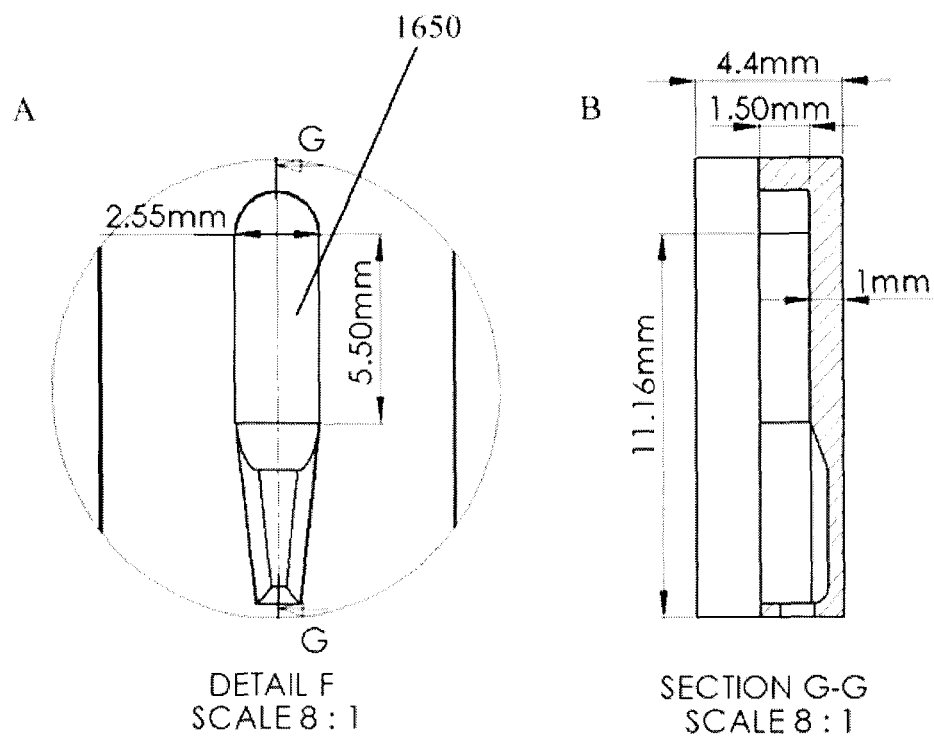
FIG. 15A illustrates a top view of a chamber of a device for holding sperm and immobilize/release oocytes in accordance to one embodiment of the present invention.
FIG. 15B illustrates a side sectional view of the sperm well illustrated in FIG. 15A through Section G-G.

The design of the sealed chamber of the device of the present invention may critically affect the generation of bubbles. Bubbles detrimentally affect oocyte imaging, making ICSI operation difficult. To reduce the risk of bubble generation, as shown in FIGS. 15A and 15B, one embodiment may be to have the corners of the chamber 1650 rounded. The effectiveness of this design approach to reduce bubble generation has been proven by the present inventors via experiments.

Figure 16:
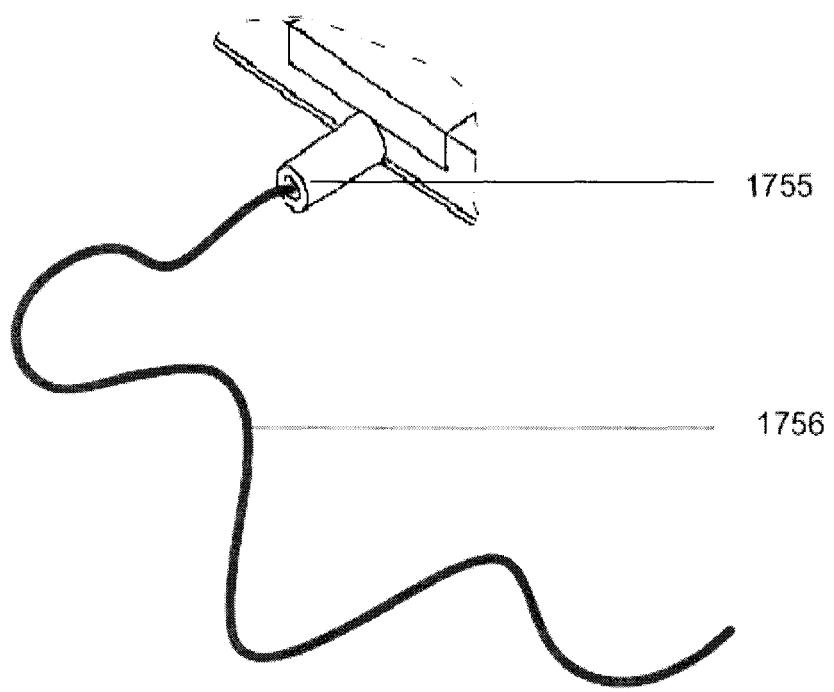
FIG. 16 illustrates the connection between an air outlet and tubing of a device for holding sperm and immobilize/release oocytes in accordance to one embodiment of the present invention.

With reference to FIG. 16 a connector or air outlet 1755 may connect the sealed chamber to a pressure pump (not shown) such as via a tube 1756. The internal diameter of the connector may be designed to fit a standard thin and flexible plastic tube, minimizing pressure disturbance caused by the accidental bending of the tube. Keeping pressure balance may also be crucial to reduce the possibility of bubble generation.

Figure 17:
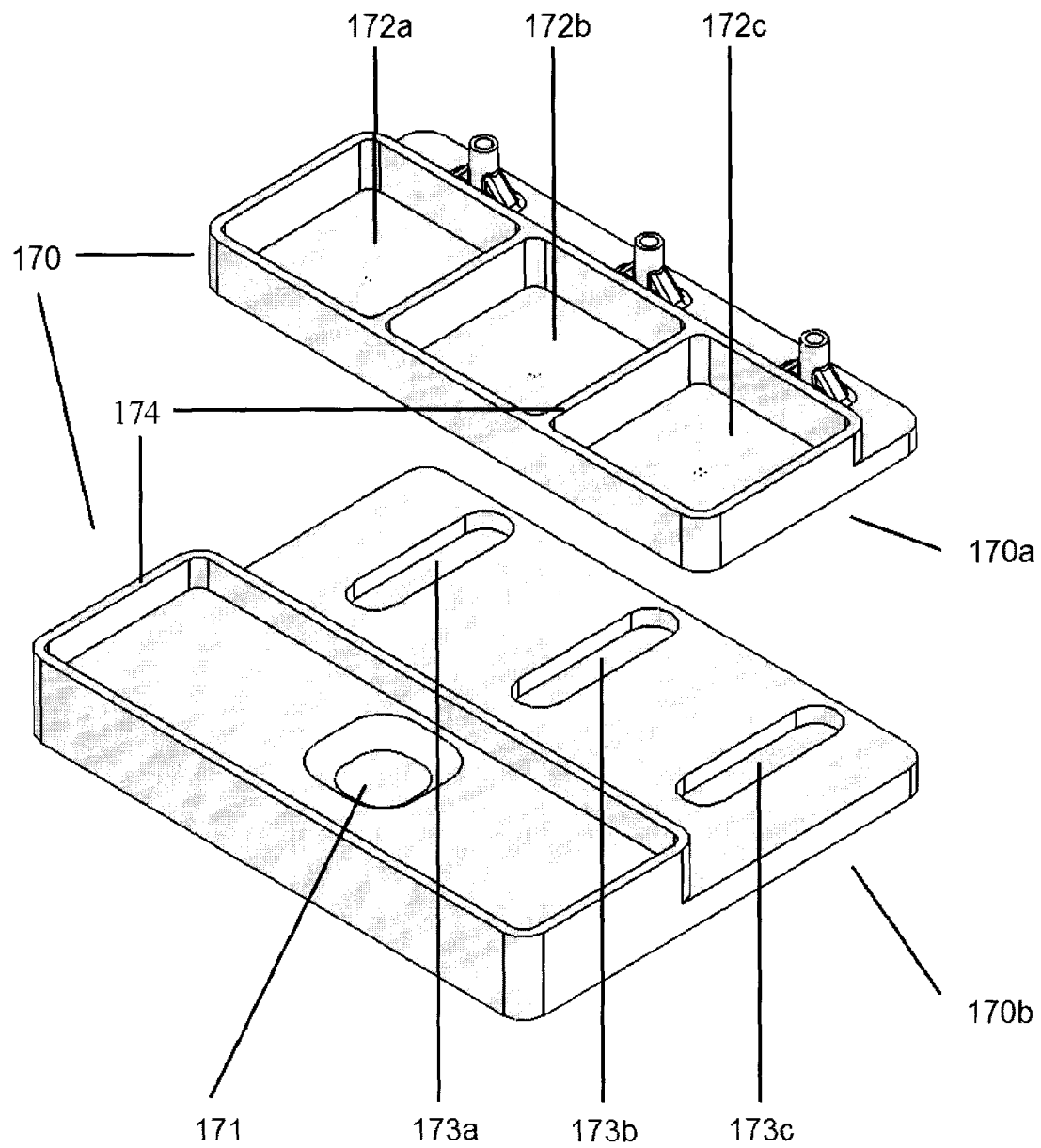
FIG. 17 illustrates the design of a sperm well of a device for holding sperm and multiple wells for immobilization/release oocytes in accordance to one embodiment of the present invention.

The device for motile cells and non-motile cells of the present invention may include more than one sperm well and/or more than one oocyte well. FIG. 17 illustrates the design a device 170 having a sperm well 171 for holding sperm and multiple wells 172a, 172b, 172c for immobilization/release oocytes. Each one of multiple wells 172a, 172b, 172c may be connected to a corresponding sealed chamber 173a, 173b, 173c. Alternatively, multiple wells may be connected to one sealed chamber (not shown). FIG. 17 illustrates a device having upper part 170a and base part 17b.

With continued reference to FIG. 17, in one embodiment, the device of the present invention may include shoulders or dams 174 around every well for the non-motile and motile cells to contain the sample carrying the non-motile and motile cells and mineral oil. Dams 174 may be useful for appropriately maintaining temperature and pH of the culture medium within the wells. It should be understood that similar dams may be included in the devices having one well for holding sperm and one well for holding oocytes similar to the device shown in FIG. 11.

Silicon is not optically transparent, and silicon microfabrication is costly. Although glass is optically transparent, processing micro features on glass is also not suitable for mass manufacturing of cell holding devices. Considering the cost and technology feasibility, injection molding may be chosen to manufacture the devices of the present invention with through holes drilled by laser technology. The two-part structures of the device of the present invention may be made separately by injection molding. The material choice may be medical grade Lexan™ that is suitable for injection molding, optically transparent and mechanical robust so an injection micropipette may not able to scratch the bottom surface of the oocyte well and sperm well. Therefore, the oocytes and sperm held on the device may be imaged clearly using the inverted microscope. The selected material may also have good thermal properties in order to withstand about 37 Celsius degrees during ICSI without significant structural deformation. This constant temperature may be kept during ICSI operation to meet the requirements of standardized ICSI operation.

Accordingly, in one embodiment, the present application provides a system for automated tracking and manipulation of a microscopic motile specimen characterized in that said system comprises: (a) a first positioner, said first positioner adapted for supporting a substrate having the motile specimen, and for controlling the motion of said substrate, said first positioner being operationally linked to a host computer; (b) a second positioner to control motion of a manipulating means for manipulating the motile specimen in the substrate, said second positioner being operationally linked to the host computer; (c) a microscope means for viewing the motile specimen in the substrate and the manipulating means, said microscope means being operationally linked to the host computer; (d) an image acquiring unit capable of being mounted on the microscope means, said image acquiring unit being operationally linked to the host computer, and said image acquiring unit capable of providing images to the host computer of the motile specimen and the manipulating means; and (e) the host computer, said host computer including means for processing the images provided by the image acquiring unit, means for motion control of the first positioner for automatically tracking the motile specimen, and means for motion control of the second positioner for automatically manipulating the motile specimen with the manipulating means.

In one embodiment of the system of the present invention, the system further comprises a pressure unit connected to the manipulating means for automatically controlling aspiration and dispensation of the motile specimen with the manipulating means, said pressure unit being operationally linked to the host computer.

In another embodiment of the system of the present invention, the system further comprises a vibration isolation table adapted for supporting the first positioner, the second positioner, the microscope means and the image acquiring unit.

In another embodiment of the system of the present invention, the first positioner is a multi-degrees-of-freedom motorized stage mounted to the microscope means.

In another embodiment of the system of the present invention, the second positioner is a multi-degrees-of-freedom motorized micromanipulator.

In another embodiment of the system of the present invention, the pressure unit comprises a motorized stage and syringe, said motorized stage configured to automatically control a piston inside the syringe.

Also provided, in another embodiment, is a method for automatically manipulating a microscopic motile specimen characterized in that said method comprises the following steps: (a) placing a substrate having the motile specimen on a first positioner mounted to a microscope means having an image acquiring unit; (b) acquiring microscopic images of the motile specimen and a micropipette means used to manipulate the motile specimen with the image acquiring unit; (c) automatically tracking the motile specimen on the substrate based on the images of the motile specimen and micropipette means using the first positioner; (d) automatically moving the micropipette means using a second positioner connected to the micropipette means to a location substantially proximal to the motile specimen; and (e) automatically immobilizing the motile specimen using the micropipette means for manipulation of the motile specimen.

In one embodiment of the method of the present invention, step (a) comprises placing a sample that includes a plurality of microscopic motile specimen on the substrate, and wherein said method further comprises selecting a target microscopic motile specimen within the sample.

In one embodiment of the previous embodiment, the selection of the target microscopic motile specimen is done automatically by a computer or manually by an operator.

In another embodiment of the method of the present invention, the microscopic motile specimen Includes a tail, and wherein the motile specimen is immobilized by automatically pressing the tail against the substrate using the micropipette means.

In one embodiment of the preceding embodiment, the method further comprises a step for automatically determining or approximating a position of the tail, and immobilizing the motile specimen based on said position.

In another embodiment of the method of the present invention, the method further comprises the step of automatically aspirating the motile specimen using a motorized pressure unit connected to the micropipette means.

In one embodiment of the embodiment of the preceding paragraph, the method further comprises selecting a desired destination within the micropipette means for the motile specimen to reach, and automatically aspirating the motile specimen to the desired destination within the micropipette means using the motorized pressure unit. In another embodiment of the embodiment of the preceding paragraph, the method further comprises automatically aspirating a plurality of motile specimens into the micropipette means. In yet another embodiment of the embodiment of the preceding paragraph, the method further comprises the step automatically dispensing the motile specimen out of the micropipette means using the motorized pressure unit connected to the micropipette means.

In another embodiment of the method of the present invention, the motile specimen is a sperm.

In another embodiment of the method of the present invention, the microscopic motile specimen includes a tall portion and a head portion, and wherein step (c) includes: calculating approximate position of the head portion, calculating approximate position of the tail portion, calculating approximate direction of movement of the microscopic motile specimen, calculating approximate speed of the microscopic motile specimen, and calculating approximate angular velocity of the microscopic motile specimen.

In another embodiment of the method of the present invention, the microscopic motile specimen is placed on the substrate by placing a sample of the microscopic motile specimen together with a culture medium in the substrate and covering the culture medium and sample with a mineral oil phase.

In one embodiment of the embodiment described in the last paragraph, the method further comprises automatically cleaning an outside surface of the micropipette means, wherein the automatically cleaning of the outside surface of the micropipette means includes the following steps: (i) automatically lifting the micropipette out of the culture medium through the mineral oil and into the air using using the second positioner, and (ii) automatically lowering the micropipette means into the culture solution using the second positioner.

In one embodiment of the embodiment described in the last paragraph, the method further comprises automatically cleaning an inside of the micropipette means by automatically expelling culture medium using a motorized pressure unit connected to the micropipette means, thereby cleaning the inside surface of the micropipette means.

Also provided, in another embodiment, is a device for holding motile cells and non-motile cells, said device comprising: (a) one or more wells capable of receiving the motile cells; (b) a sealed chamber having an air outlet; and (c) one or more wells capable of receiving the non-motile cells, each of the one or more wells for non-motile cells including an array of through holes operable for holding the non-motile cells, each through hole in the array having openings on opposing ends, said through holes connecting the well for non-motile cells to the sealed chamber.

In one embodiment of the device of the present invention, the motile and non-motile cells are provided in a culture medium, and wherein the device Includes one or multiple dams around each well for the motile and non-motile cells, said one or multiple dams capable of containing a substance suitable for maintaining the temperature and pH of the culture medium.

In another embodiment of the device of the present invention, the device is manufactured into two or more parts, said two or more parts being configured to be assembled into the device.

In another embodiment of the device of the present invention, the device comprises an assembly having at least two parts, one part including the one or more wells capable of receiving the non-motile cells, and another part including the one or more wells capable of receiving the motile cells.

In another embodiment of the device of the present invention, the device is disposable.

In another embodiment of the device of the present invention, the center of each of the one or more wells for the non-motile cells is configured to be substantially close to a rotational axis of the device.

In another embodiment of the device of the present invention, the one or more wells for the motile cells and the one or more wells for the non-motile cells include sloped walls.

In another embodiment of the device of the present invention, the device is fabricated from optically transparent material.

In another embodiment of the device of the present invention, the device is configured for use with an inverted microscope.

In another embodiment of the device of the present invention, the one or more wells for motile cells is operationally close to the one or more wells for the non-motile cells.

In another embodiment of the device of the present invention, the sealed chamber comprises rounded corners.

In another embodiment of the device of the present invention, the bottom surface defines a slope, and wherein the air outlet is positioned higher than the slope.

In another embodiment of the device of the present invention, the motile cells are sperms and said non-motile cells are oocytes.

In another embodiment of the device of the present Invention, the device is configured for use in intracytoplasmic sperm injection or other microinjection procedures.

It will be appreciated by those skilled in the art that other variations of the one or more embodiments described herein are possible and may be practiced without departing from the scope of the present invention.

We claim:

1. A method of automatically manipulating a sperm cell, said method comprising the following steps:
   (a) placing a substrate having a plurality of sperm cells on a first positioner mounted to a microscope means having a camera, the camera having a field of view, said first positioner for controlling the motion of said substrate and being operationally linked to a host computer having a computerized processor;
   (b) acquiring with the camera microscopic images of the sperm cell and of a micropipette means used to manipulate the sperm cell;
   (c) using the microscopic images of the plurality of sperm cells to automatically or manually select a sperm cell within the plurality of sperm cells;
   (d) automatically tracking in real time the sperm cell on the substrate based on the images of the sperm cell and positioning the sperm cell using the first positioner, said automatic tracking of the sperm cell in real time comprising, for every consecutive image captured by the camera, a computerized processor registering a distance from a head of the sperm cell to a center of the field of view of the camera, and the computerized processor using the distance as input to move the first positioner and adjust the distance from the head of the sperm cell to the center of the field of view to zero, such that the sperm cell head is kept at a center of the field of view of the camera;
   (e) automatically locating a position of the sperm cell's tail in real time, said locating of the sperm cell's tail position comprising: (i) for consecutive images captured by the camera the computerized processor registering an average direction of movement of the sperm cell and the computerized processor adding said average direction of movement to each spatial component of the sperm head position thereby obtaining a sperm tail region of interest (STROI), (ii) for consecutive images captured by the camera, the computerized processor obtaining an absolute difference between STROI thereby enhancing the STROI, and (iii) the computerized processor finding a maximum intensity sub-region in the STROI whereby the maximum intensity sub-region in the STROI represents the sperm tail position;

(f) automatically moving the micropipette means using a second positioner connected to the micropipette means to a location substantially proximal to the tail position of the sperm cell; and (g) automatically pressing the tail of the sperm against the substrate with the micropipette means thereby immobilizing the sperm cell using the micropipette means for manipulation of the sperm cell.

2. The method of claim 1, wherein said method further comprises automatically immobilizing more than one sperm cells and the step of automatically aspirating the more than one sperm cells into the micropipette means of step (g) using a motorized pressure unit connected to the micropipette means, and wherein the motorized pressure unit includes a syringe and a motorized stage.

3. The method of claim 2, wherein said method further comprises positioning each one of the more than one sperm cells at a desired position inside the micropiette means and at an approximately eaual distance from one another within the micropipette means using the motorized pressure unit.

4. The method of claim 3, wherein said method further comprises the step automatically dispensing only one sperm cell of the more than one sperm cells out of the micropipette means using the motorized pressure unit connected to the micropipette means.

5. The method of claim 1, wherein said plurality of sperm cells are provided in a culture medium and a mineral oil phase covering the culture medium and the sperm cell, and wherein said method further comprises automatically cleaning an outside surface of the micropipette means, wherein said automatically cleaning of the outside surface of the micropipette means includes the following steps: (i) automatically lifting the micropipette out of the culture medium through the mineral oil and into the air using the second positioner, and (ii) automatically lowering the micropipette means into the culture solution using the second positioner.

6. The method of claim 1, wherein said plurality of sperm cells are provided in a culture medium, and wherein said method further comprises automatically cleaning an inside of the micropipette means by automatically expelling culture medium from within the micropipette means using a motorized pressure unit connected to the micropipette means, thereby cleaning the inside surface of the micropipette means.

* * * * *